US00PP27829P3

(12) United States Plant Patent
Grosser

(10) Patent No.: US PP27,829 P3
(45) Date of Patent: Apr. 4, 2017

(54) SWEET ORANGE TREE NAMED 'OLL-4'

(50) Latin Name: *Citrus sinensis*
Varietal Denomination: OLL-4

(71) Applicant: Florida Foundation Seed Producers, Inc., Marianna, FL (US)

(72) Inventor: Jude W. Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 3 days.

(21) Appl. No.: 14/121,859

(22) Filed: Oct. 27, 2014

(65) Prior Publication Data

US 2016/0120083 P1 Apr. 28, 2016

(51) Int. Cl.
*A01H 5/08* (2006.01)

(52) U.S. Cl.
USPC ..... Plt./202

(58) Field of Classification Search
USPC ..... Plt./202, 201
See application file for complete search history.

(56) References Cited

U.S. PATENT DOCUMENTS

| | | | |
|---|---|---|---|
| PP21,224 | P2 | 8/2010 | Grosser et al. |
| PP21,356 | P3 | 10/2010 | Gmitter, Jr. et al. |
| PP21,535 | P2 | 11/2010 | Grosser et al. |
| 2013/0276180 | P1 | 10/2013 | Grosser |
| 2015/0052645 | P1 | 2/2015 | Grosser |

OTHER PUBLICATIONS

U.S. Appl. No. 13/987,563, filed Aug. 7, 2013, Grosser.
U.S. Appl. No. 13/987,609, filed Aug. 13, 2013, Grosser.
Grosser et al., "Highlights from the UF/IFAS/CREC Citrus Improvement Program," presentation at the Florida Citrus Show, Ft. Pierce, Florida, Jan. 19-20, 2011.
Grosser et al., "Somaclonal Variation in Sweet Orange: Practical Applications for Variety Improvement and Possible Causes," pp. 219-234, in: Kahn, I.H. (Ed.). Citrus Genetics, Breeding and Biotechnology, CAB International, 2007.
Larkin et al., "Somaclonal variation—a novel source of variability from cell cultures for plant improvement," *Theoret Appl Genet* 60:197-214, 1981.

*Primary Examiner* — June Hwu
(74) *Attorney, Agent, or Firm* — Dentons US LLP

(57) ABSTRACT

A new and distinct sweet orange clone, 'OLL-4' was produced via embryonic callus (tissue culture) from an original tree selection ('OLL') from an abandoned USDA field trial. 'OLL-4' produces easy-to-peel, round oranges with excellent internal and external color. Trees of 'OLL-4' exhibit improved cold and drought tolerance over industry standard oranges, and do not seem to exhibit alternate bearing.

4 Drawing Sheets

Latin name of the genus and species of the plant claimed: *Citrus sinensis.*

Variety denomination: 'OLL-4'.

BACKGROUND OF THE INVENTION

The present invention relates to a new and distinct variety of sweet orange tree named 'OLL-4'. 'OLL-4' is a somaclone regenerated from embryogenic callus (tissue culture) of 'OLL' ('Orie Lee Late') sweet orange, with high-quality fruit that usually matures in the standard 'Valencia' time period. 'OLL' (unpatented) is believed to be an irradiation-induced mutant line originating from 'Pineapple' sweet orange in an abandoned USDA trial attempting to generate a seedless 'Pineapple' orange. 'OLL' attracted attention because it never dropped fruit, a serious problem with 'Pineapple', and held quality late into the summer. Propagations of 'OLL' were not uniform and included some trees of poor growth and productivity, as well as robust high-yielding trees. In efforts to generate genetically stable clones from the 'OLL' selection, tissue cultures (embryogenic callus) were established for the creation of somaclones. At present, 'OLL-4' has been the highest yielding somaclone, and is the only remaining somaclone showing no Huanglongbing (HLB) disease symptoms. Trees of 'OLL-4' sweet orange topworked onto HLB-infected root/scaffold trees ('Swingle' and 'Carrizo') are also growing off quite well, but it is too early to determine the actual level of HLB tolerance. Topworked trees demonstrated true-to-typeness, as well as new trees grafted to experimental rootstocks also planted at St. Cloud, Fla.

The first asexual reproduction of the claimed tree occurred in Lake Alfred, Fla., in which original trees of 'Hamlin' sweet orange grafted onto 'Carrizo' citrange rootstock were topworked with 'OLL-4' in spring of 2013. Those trees produced true-to-type 'OLL-4' fruit.

SUMMARY OF THE INVENTION

'OLL-4' produces round oranges with internal and external color similar to that of 'Rhode Red Valencia' (Table 1). Fruit of 'OLL-4' holds on the tree exceptionally well, and maintains quality into the summer. Fruit of 'OLL-4', like all of the 'OLL' oranges, peel easier than 'Valencia', which, combined with the attractive external color, provides excellent crossover potential as fresh fruit, thereby expanding the available fresh orange portfolio for Florida. 'OLL' seedling trees (including 'OLL-4') have shown good drought tolerance in the greenhouse, as overgrown trees in small pots rarely wilt compared to other sweet orange seedlings. This apparent improved stress tolerance may be useful against HLB disease. Limited yield data is available, but the original tree of 'OLL-4' has been the highest yielding tree among the 'OLL' somaclones over the past 3 years, producing more than five 90-lb. boxes of fruit per year, with a maximum of 6.13 boxes in 2014 (Table 1). Trees on 'Swingle' citrumelo appear to yield more than standard 'Valencia'. Production of lbs solids on 'OLL-4' is not the highest among the 'OLL' somaclones (Table 2), but has been as good as compared to traditional 'Valencia'. 'OLL' oranges, including 'OLL-4', have not exhibited the undesirable low ratios associated with 'Valencia' during the past two seasons (Tables 2 and 3). Alternate bearing has not been an issue on 'OLL-4'. Sensory (taste panel) analyses have indicated that 'OLL-4' has a favorable 'Valencia'-like flavor profile (Table 3). Top-worked and grafted trees of 'OLL-4' on various rootstocks are growing off quite well.

TABLE 1

Yield data from original 'OLL' somaclone trees on 'Swingle' citrumelo planted in 2001 (90 lb. boxes)

| | 2012 BOXES | 2013 BOXES | 2014 BOXES | TOTAL BOXES | AVG. BOXES |
|---|---|---|---|---|---|
| OLL-1 | 4.00 | 4.75 | 3.88 | 12.63 | 4.21 |
| OLL-2 | 3.00 | 3.75 | 2.34 | 9.09 | 3.03 |
| OLL-3 | 2.75 | 4.75 | 4.13 | 11.63 | 3.88 |
| OLL-4 | 5.75 | 5.25 | 6.13 | 17.13 | 5.71 |
| OLL-5 | 4.75 | 3.75 | 3.38 | 11.88 | 3.96 |
| OLL-6 | 2.75 | 2.75 | 5.88 | 11.38 | 3.79 |
| OLL-7 | 2.75 | 4.25 | 3.88 | 10.88 | 3.63 |
| OLL-8 | 1.75 | 0.00 | 0.00 | 1.75 | 0.58 |
| OLL-9 | 4.25 | 4.00 | 3.13 | 11.38 | 3.79 |
| OLL-10 | 5.00 | 5.75 | 5.38 | 16.13 | 5.38 |
| OLL-11 | 1.00 | 1.50 | 1.38 | 3.88 | 1.29 |
| OLL-15 | 2.00 | 2.75 | 2.88 | 7.63 | 2.54 |
| OLL-16 | 3.00 | 3.75 | 2.63 | 9.38 | 3.13 |
| OLL-19 | 4.00 | 5.00 | 3.88 | 12.88 | 4.29 |
| OLL-20 | 2.00 | 5.25 | 4.13 | 11.38 | 3.79 |
| OLL-21 | 3.75 | 4.75 | 4.13 | 12.63 | 4.21 |
| OLL-22 | 5.25 | 4.50 | 3.38 | 13.13 | 4.38 |
| OLL-23 | 3.75 | 6.75 | 3.88 | 14.38 | 4.79 |
| OLL-25 | 3.25 | 3.75 | 2.38 | 9.38 | 3.13 |
| OLL-27 | 4.25 | 4.50 | 5.38 | 14.13 | 4.71 |

TABLE 2

Juice Quality Data from 'OLL'-Series Somaclones (data from Mar. 2, 2012).

| Variety | Lbs. Juice Per Box | Acid | Total Brix | Ratio | Lbs. Solids Per Box | Color |
|---|---|---|---|---|---|---|
| 'Valencia' | 54.41 | 1.00 | 12.03 | 12.03 | 6.55 | 38.60 |
| 'OLL 20' | 53.23 | 0.84 | 12.10 | 14.40 | 6.44 | 40.50 |
| 'OLL 27' | 54.99 | 0.84 | 12.34 | 14.69 | 6.79 | 39.80 |
| 'OLL 25' | 57.58 | 0.79 | 12.81 | 16.22 | 7.38 | 40.20 |
| 'OLL 9' | 56.30 | 0.94 | 12.97 | 13.80 | 7.30 | 39.90 |
| 'OLL 15' | 49.48 | 0.99 | 14.56 | 14.71 | 7.20 | 39.50 |
| 'OLL 2' | 51.55 | 0.77 | 12.77 | 16.58 | 6.58 | 41.00 |
| 'OLL 3' | 54.52 | 0.98 | 12.92 | 13.18 | 7.04 | 40.30 |
| 'OLL 4' | 55.52 | 0.92 | 12.60 | 13.70 | 7.00 | 40.70 |
| 'OLL 7' | 57.51 | 0.94 | 13.20 | 14.04 | 7.59 | 41.20 |
| 'Swingle' Control | 48.46 | 0.79 | 12.91 | 16.34 | 6.26 | 39.10 |

TABLE 2-continued

Juice Quality Data from 'OLL'-Series Somaclones (data from Mar. 2, 2012).

| Variety | Lbs. Juice Per Box | Acid | Total Brix | Ratio | Lbs. Solids Per Box | Color |
|---|---|---|---|---|---|---|
| 'OLL 21' | 58.20 | 0.77 | 12.38 | 16.08 | 7.20 | 40.30 |
| 'OLL 10' | 55.55 | 0.82 | 12.42 | 15.15 | 6.90 | 40.60 |
| 'OLL 5' | 53.92 | 0.93 | 13.13 | 14.12 | 7.08 | 40.10 |
| 'OLL 23' | 57.21 | 0.81 | 12.12 | 14.96 | 6.93 | 39.90 |
| 'OLL 19' | 54.02 | 0.84 | 12.32 | 14.67 | 6.65 | 40.90 |
| 'OLL 1' | 55.10 | 0.90 | 12.90 | 14.33 | 7.11 | 41.50 |
| 'OLL 3-9' | 58.19 | 0.96 | 12.85 | 13.39 | 7.48 | 40.80 |
| 'OLL 3-10' dwarf | 53.80 | 0.80 | 12.51 | 15.64 | 6.73 | 41.20 |
| 'OLL 8' | 56.43 | 0.77 | 11.99 | 15.57 | 6.77 | 40.70 |

TABLE 3

Sensory analysis of Not From Concentrate (NFC) juice from OLL oranges and 'Valencia'control.

| ANALYSIS DATE | SAMPLE ID | BRIX COR. | ACID % | RATIO | pH |
|---|---|---|---|---|---|
| Mar. 21, 2014 | OLL #10 | 12.97 | 0.88 | 14.74 | 3.78 |
| Mar. 21, 2014 | OLL #11 | 12.37 | 0.85 | 14.55 | 3.77 |
| Mar. 21, 2014 | OLL #27 | 12.53 | 0.87 | 14.41 | 3.77 |
| Mar. 21, 2014 | OLL #8 | 13.26 | 0.97 | 13.67 | 3.75 |
| Mar. 21, 2014 | OLL #2 | 12.09 | 0.81 | 14.93 | 3.85 |
| Mar. 21, 2014 | OLL #20 | 12.42 | 0.89 | 13.96 | 3.77 |
| Mar. 21, 2014 | OLL #7 | 12.71 | 0.85 | 14.95 | 3.83 |
| Mar. 21, 2014 | OLL #6 | 12.10 | 0.87 | 13.91 | 3.80 |
| Mar. 21, 2014 | OLL #1 | 12.47 | 0.95 | 13.13 | 3.73 |
| Mar. 21, 2014 | OLL #16 | 12.34 | 0.87 | 14.18 | 3.75 |
| Mar. 21, 2014 | OLL #5 | 11.16 | 0.77 | 14.49 | 3.90 |
| Mar. 21, 2014 | OLL #21 | 11.69 | 0.87 | 13.44 | 3.82 |
| Mar. 21, 2014 | OLL #25 | 13.36 | 0.87 | 15.36 | 3.72 |
| Mar. 21, 2014 | OLL #19 | 12.80 | 0.81 | 15.80 | 3.84 |
| Mar. 21, 2014 | OLL #4 | 12.54 | 0.85 | 14.75 | 3.84 |
| Mar. 21, 2014 | N10-25 | 12.96 | 0.93 | 13.94 | 3.76 |
| Mar. 21, 2014 | OLL #9 | 12.59 | 0.85 | 14.81 | 3.80 |
| Mar. 21, 2014 | Valencia | 12.07 | 0.95 | 12.71 | 3.69 |
| Mar. 21, 2014 | OLL #23 | 11.55 | 0.76 | 15.20 | 3.88 |
| Mar. 21, 2014 | OLL #3 | 12.37 | 0.91 | 13.59 | 3.72 |

| ANALYSIS DATE | SAMPLE ID | COLOR | OIL % | SINKING PULP |
|---|---|---|---|---|
| Mar. 21, 2014 | OLL #10 | 39.53 | 0.016 | 14.0 |
| Mar. 21, 2014 | OLL #11 | 40.50 | 0.012 | 12.0 |
| Mar. 21, 2014 | OLL #27 | 40.62 | 0.012 | 12.0 |
| Mar. 21, 2014 | OLL #8 | 39.30 | 0.014 | 12.0 |
| Mar. 21, 2014 | OLL #2 | 10.50 | 0.012 | 12.0 |
| Mar. 21, 2014 | OLL #20 | 40.09 | 0.015 | 14.0 |
| Mar. 21, 2014 | OLL #7 | 40.81 | 0.013 | 12.0 |
| Mar. 21, 2014 | OLL #6 | 40.58 | 0.012 | 12.0 |
| Mar. 21, 2014 | OLL #1 | 40.48 | 0.011 | 12.0 |
| Mar. 21, 2014 | OLL #16 | 40.25 | 0.015 | 12.0 |
| Mar. 21, 2014 | OLL #5 | 41.09 | 0.011 | 10.0 |
| Mar. 21, 2014 | OLL #21 | 40.63 | 0.013 | 12.0 |
| Mar. 21, 2014 | OLL #25 | 40.16 | 0.018 | 12.0 |
| Mar. 21, 2014 | OLL #19 | 40.59 | 0.017 | 12.0 |
| Mar. 21, 2014 | OLL #4 | 40.74 | 0.015 | 12.0 |
| Mar. 21, 2014 | N10-25 | 38.67 | 0.020 | 14.0 |
| Mar. 21, 2014 | OLL #9 | 40.81 | 0.013 | 12.0 |
| Mar. 21, 2014 | Valencia | 38.45 | 0.012 | 10.0 |
| Mar. 21, 2014 | OLL #23 | 40.69 | 0.012 | 10.0 |
| Mar. 21, 2014 | OLL #3 | 40.12 | 0.015 | 12.0 |

| ANALYSIS DATE | SAMPLE ID | VIT.C (mg/100 ml) | Limonin ppm | Avg. Overall Flavor Score |
|---|---|---|---|---|
| Mar. 21, 2014 | OLL #10 | 53.79 | 2.5 | 3.33 |
| Mar. 21, 2014 | OLL #11 | 45.27 | 2.1 | 3.25 |
| Mar. 21, 2014 | OLL #27 | 42.65 | 1.1 | 3.25 |

TABLE 3-continued

Sensory analysis of Not From Concentrate (NFC) juice from OLL oranges and 'Valencia'control.

| | | | | |
|---|---|---|---|---|
| Mar. 21, 2014 | OLL #8 | 52.55 | 2.6 | 3.33 |
| Mar. 21, 2014 | OLL #2 | 44.24 | 1.9 | 3.33 |
| Mar. 21, 2014 | OLL #20 | 48.68 | 1.3 | 3.25 |
| Mar. 21, 2014 | OLL #7 | 38.54 | 1.3 | 3.25 |
| Mar. 21, 2014 | OLL #6 | 40.55 | 1.4 | 3.25 |
| Mar. 21, 2014 | OLL #1 | 45.95 | 2.2 | 3.42 |
| Mar. 21, 2014 | OLL #16 | 44.47 | 1.6 | 3.50 |
| Mar. 21, 2014 | OLL #5 | 35.07 | 2.2 | 3.42 |
| Mar. 21, 2014 | OLL #21 | 38.34 | 2.5 | 3.42 |
| Mar. 21, 2014 | OLL #25 | 42.21 | 1.5 | 3.42 |
| Mar. 21, 2014 | OLL #19 | 42.34 | 2.0 | 3.50 |
| Mar. 21, 2014 | OLL #4 | 40.04 | 1.0 | 3.25 |
| Mar. 21, 2014 | N10-25 | 41.89 | 1.0 | 3.33 |
| Mar. 21, 2014 | OLL #9 | 38.35 | 1.4 | 3.25 |
| Mar. 21, 2014 | Valencia | 40.35 | 0.8 | 3.42 |
| Mar. 21, 2014 | OLL #23 | 34.54 | 0.9 | 3.25 |
| Mar. 21, 2014 | OLL #3 | 40.30 | 3.0 | 3.58 |

BRIEF DESCRIPTION OF THE DRAWINGS

'OLL-4' is illustrated by the accompanying photographs, which show the tree's form, foliage and fruit. The colors shown are as true as can be reasonably obtained by conventional photographic procedures. The photographs are of a tree approximately 13 years old.

DETAILED BOTANICAL DESCRIPTION

Phenotypic Description of *Citrus sinensis* 'OLL-4'

Figure 1:
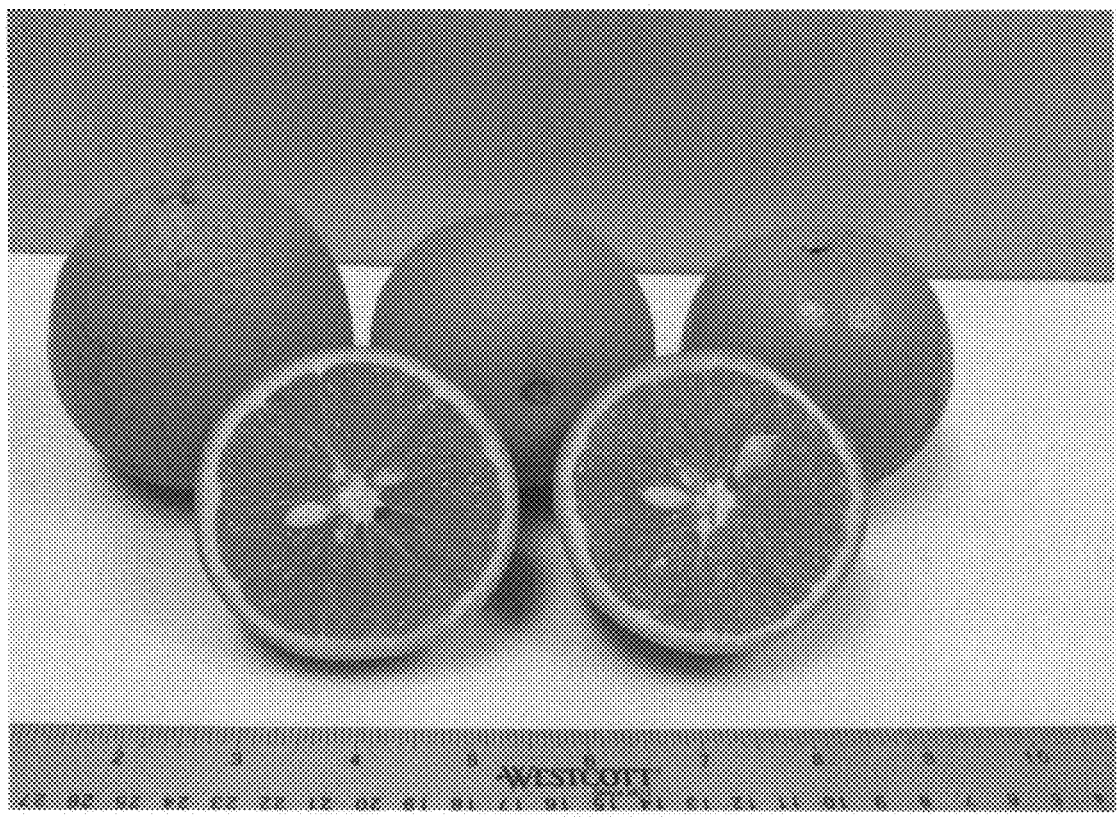
FIG. 1—Shows the internal and external appearance of the fruit.
Figure 2:
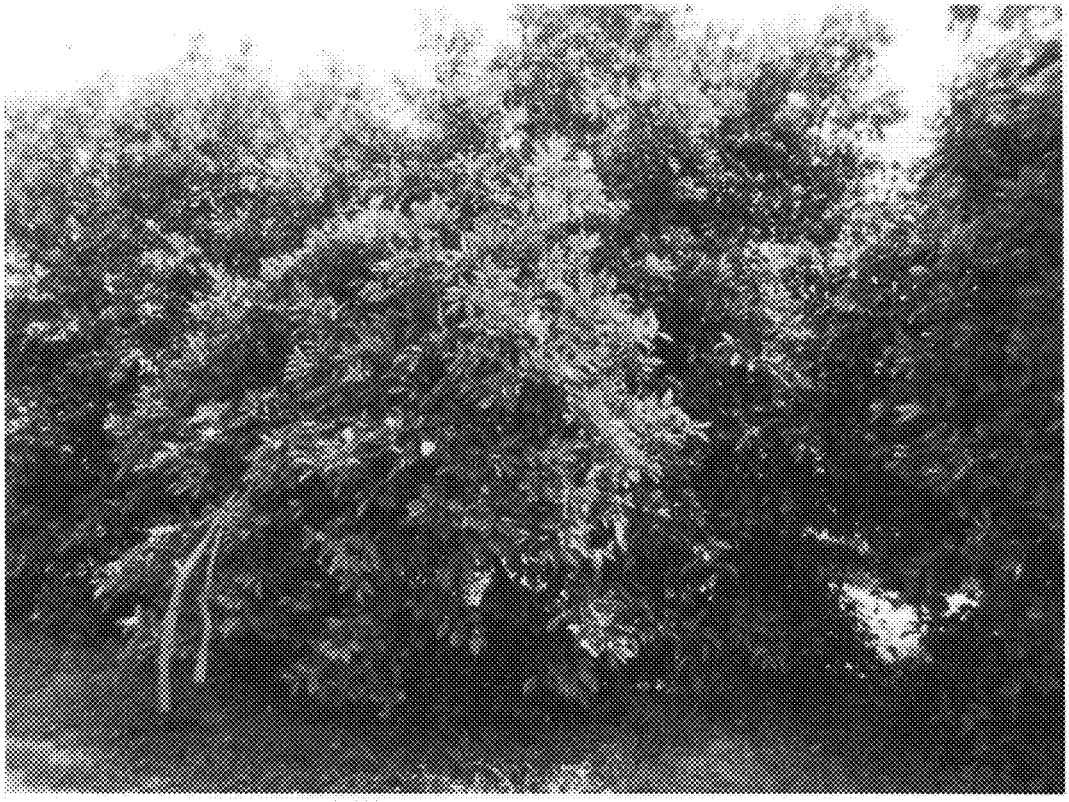
FIG. 2—Shows the overall mature plant growth habit in the spring time.
Figure 3:
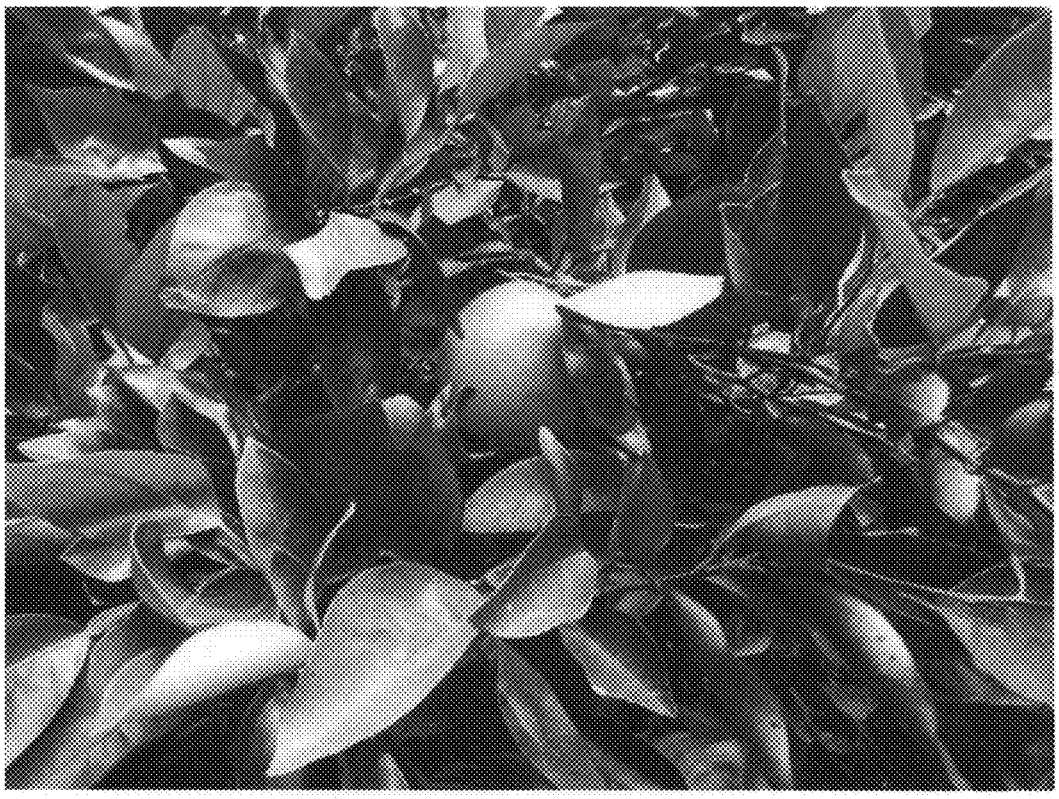
FIG. 3—Shows a close-up of leaves and a mature fruit.
Figure 4:
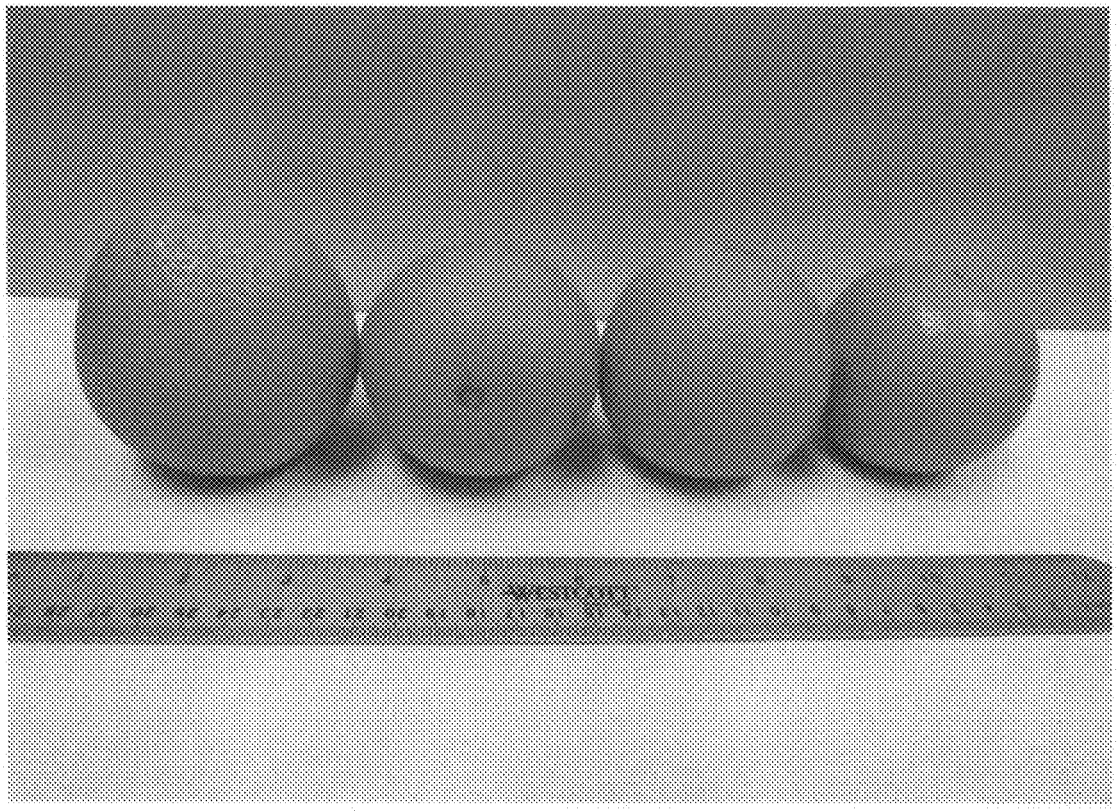
FIG. 4—Shows a close-up of the mature fruit.

The following detailed description sets forth the distinctive characteristics of 'OLL-4'. The present botanical description is that of the variety grown on a 13-year-old tree growing on 'Swingle' citrumelo rootstock (*C. paradisi*× *Poncirus trifoliata*) at St. Cloud experimental block, and a top-worked tree at the same location. The colors (except those in common terms) are described from the R.H.S. Colour Chart published by The Royal Horticultural Society in London (Fifth Edition), in association with the Flower Council of Holland.

Classification:

*Botanical.*—*Citrus sinensis* (putative).

*Common name.*—Sweet orange.

Parentage:

*Female parent.*—'OLL' ('Orie Lee Late') sweet orange tree (unpatented).

*Male parent.*—N/A.

Tree:

*Ploidy.*—Diploid.

*Size.*—Medium large.

*Tree height.*—5.8 m.

*Tree spread.*—5.0 to 5.5 m.

*Vigor.*—Vigorous.

*Density.*—Canopies are quite dense.

*Form.*—The tree is obloid shaped with both lateral and upright branches growing; branches with fruit exhibit drooping.

*Growth habit.*—Both upright and lateral growth with low medium angle.

Trunk:

*Trunk diameter.*—17.8 cm in diameter at 30 cm above the ground, 16-year-old tree.

*Trunk texture.*—Smooth.

*Trunk bark color.*—RHS 199C (greyed-brown); irregularly striated with RHS 189A (greyed-green).

Branches:

*Crotch angle.*—First crotch forms a 60 to 65-degree angle, middle crotch forms a 35-degree angle.

*Branch length.*—Branch reaches 5.6 meters from the first crotch to the tip of the branch.

*Branch texture.*—Relatively smooth, occasionally with small thorns or spines.

*Branch color* (*shoots from previous flush, hardened, and* 4 *to* 5 mm *in diameter*).—RHS 137A (green).

*Spines.*—Spines are observed, but are primarily restricted to main scaffold branches. As trees mature, the spines diminish and do not interfere with harvest. Spine size: On mature branches, average 20 to 45 mm in length, and 2 to 4 mm in diameter at the base. Spine color: RHS 138A (green), with RHS 197A (greyed-green) at spine tip.

Leaves

*Size* (*lamina average*).—Length: 120 mm. Width: 57.8 mm.

*L/W ratio.*—2.1.

*Thickness.*—Regular and average compared to commercial sweet orange hybrids.

*Type.*—Simple.

*Shape.*—Elliptical.

*Apex.*—Retuse.

*Base.*—Acute to sub-obtuse.

*Margin.*—Entire and smooth undulate.

*Surface.*—Upper surface: Glabrous. Lower surface: Medium veins that are pinnately netted.

*Color.*—Upper surface (adaxial): RHS 137A (green). Lower surface (abaxial): RHS 143C (green).

*Petiole.*—Shape: Brevipetiolate (shorter than leaf lamina); junction between petiole and lamina is articulate. Width (petiole wing): Narrow. Shape (petiole wing): Obovate. Length: 25.5 to 26 mm. Width: 7.2 to 7.3 mm. Color: RHS 137A (green).

Flowers and flower buds:

*Type.*—Hermaphrodite.

*Bearing.*—Flowers grow from leaf axillaries and leaf terminals in small clusters or as individuals. Each flower branch consists of 4-12 flowers.

*Flower diameter.*—Fully open flower with an average diameter of 34.4 to 35 mm.

*Flower depth.*—Typical flower has an average depth of 20 mm.

*Blooming period.*—First bloom: Observed Mar. 20, 2014. Full bloom: Observed Mar. 28, 2014.

*Flower bud size.*—Length: Initial visible flower bud is 3.5 mm in length; mature flower bud is 16.6 mm in length. Diameter: Initial visible flower bud is 2.5 mm in diameter; mature flower bud is 7.1 mm in diameter.

*Flower bud shape.*—Initial visible flower bud has a slightly elongated ball shape; mature flower has an elongated olive shape.

*Color.*—RHS 144D (yellow-green) for initial visible flower bud; RHS NN155D (white) for mature flower bud with RHS 149D (yellow-green) spots distributed at the tip of the flower bud.

*Flower petals*.—Number: 5. Length: 20 mm. Width: 7.3. Shape: Flat, spatula shaped. Apex shape: Smooth, acute shaped. Base shape: Even obtuse.

*Color*.—Upper surface: RHS NN155D (white). Lower surface: RHS NN155C (white) with RHS 149D (yellow-green) spots distributed toward to the petal apex. Margin: Smooth.

*Sepal*.—Number (per flower): 5 per flower. Shape: Delta shaped with an acute angle at apex. Length: 3.8 mm. Width: 3.5 mm. Apex shape: Triangle shaped. Margin: Smooth.

*Color*.—Upper surface: RHS 145D (yellow-green). Lower surface: RHS 145C (yellow-green).

*Pedicel*.—Number: 1. Length: 6.7 to 6.8 mm. Diameter: 1.4 to 1.5 mm. Color: RHS 145B (yellow-green).

*Reproductive organs*.—Fertility: Appears self-fertile. Stamen length: 12.5 to 12.7 mm. Anther. Length: 3.4 mm. Width: 1.1 to 1.2 mm. Color: RHS 12C (yellow). Filament length: 10.2 to 10.3 mm. Pollen amount: Abundant. Pollen color (general): RHS 14A (yellow).

*Pistil*.—Number: 1. Length: 12.0 to 12.8 mm. Color: RHS 145C (yellow-green).

*Style length*.—9.5 mm.

*Style diameter*.—1.3 to 1.4 mm.

*Style color*.—RHS 145C (yellow-green).

*Ovary shape*.—Oval shaped.

*Ovary diameter*.—2.3 mm.

*Ovary color*.—RHS 145B (yellow-green).

*Fragrance*.—Fragrant.

Fruit:

*Average weight* (*per individual fruit*).—222.3 g.

*Size*.—Uniform.

*Width*.—74 to 77 mm on average.

*Length*.—82.5 to 83.3 mm on average.

*Shape*.—Fruit can be round, oval, or oblate in shape.

*Shape* (*cross-section*).—Round.

*Apex*.—Truncated.

*Apex cavity diameter*.—N/A.

*Base*.—No neck, with wrinkle at the shoulder area.

*Base cavity diameter*.—6.3 to 6.4 mm.

*Harvesting*.—First harvest can usually occur at the beginning of March (based on season and rootstock); last harvest can go into June, as fruit continue to hold on the tree for a long time with good quality.

*Fruit stem* (*short stem connecting the fruit*).—Length: 10.8 mm. Diameter: 3.8 mm. Color: RHS 196A (greyed-green with RHS 137A (green) strip.

*Fruit core*.—Spongy white fruit core (155D white group), with diameters ranging from 8 to 13 mm.

Skin:

*Adherence*.—Adherence between albedo (mesocarp) and flesh (endocarp) is strong. The adherence is evenly distributed from based to apex.

*Thickness*.—4.4 to 4.5 mm on average.

*Texture*.—Smooth.

*Color*.—Flavedo (epicarp): Ranges between RHS 21A (yellow-orange) to RHS 21C (yellow-orange). Albedo (mesocarp): RHS 11D (yellow). Stylar end: Closed.

*Rind oil cell density*.—208 oil cells/square cm.

*Oil glands*.—Appear to be distributed evenly throughout most of the fruit flavedo, with interspersed large oil glands, and with small oil glands toward the fruit shoulder area; no pitting or pebbling has been observed on the oil glands.

Flesh:

*Number of segments*.—Average between 10 and 11 segments per fruit.

*Segment walls*.—Medium soft with sufficient strength to maintain integrity as separated.

*Juice*.—Abundant.

*Color*.—Uniformly RHS 24A (orange).

*Texture*.—Medium soft.

*Vesicles*.—Length: arranged from 16.3 to 16.9 mm on average.

*Diameter* (*thickness*).—2.7 to 3.2 mm on average.

*Eating quality* (*tested at the beginning of March, varies from season to season*).—Soluble solids (average): 12.6 Brix. Acidity (average): 0.92%. Sugar/Acid Ratio: 13.7.

Seeds:

*Type*.—Mostly polyembryonic and occasionally monoembryonic.

*Number*.—Ranges from 2 to 5; occasionally some fruit contains less than 2 seeds.

*Shape*.—Seed shapes are not uniform; normal seeds are mostly ventricose/swollen shaped and clavate club shaped.

*Size*.—Length: 15.4 to 15.5 mm. Width: 8.9 to 9.0 mm.

*Seed coat color*.—Outer Surface: RHS NN155A (white) and smooth. Inner surface: RHS 165C (greyed-orange).

*Cotyledon color*.—RHS 157D (green-white).

Market use: Fruit are excellent for NFC (not from concentrate) or frozen concentrate orange juice, and also very good as a fresh market orange.

Resistance to disease: No obvious tree-debilitating disease problems have been observed in the trees or fruit of 'OLL-4' currently growing, but systematic resistance testing has not been performed. 'OLL-4' may be moderately susceptible to *citrus* canker, although canker has not been observed on 'OLL-4'.

What is claimed is:

1. A new and distinct cultivar of sweet orange tree as illustrated and described herein.

* * * * *